United States Patent [19]

Hadwiger

[11] Patent Number: 4,886,541
[45] Date of Patent: Dec. 12, 1989

[54] METHOD FOR TREATING CEREAL CROP SEED WITH CHITOSAN TO ENHANCE YIELD, ROOT GROWTH AND STEM STRENGTH

[75] Inventor: Lee A. Hadwiger, Pullman, Wash.

[73] Assignee: Washington State University Research Foundation, Pullman, Wash.

[21] Appl. No.: 198,677

[22] Filed: May 25, 1988

Related U.S. Application Data

[63] Continuation of Ser. No. 795, 702, Nov. 5, 1985 abandoned, which is a continuation of Ser. No. 658, 084, Oct. 5, 1984 abandoned.

[51] Int. Cl.$^4$ .................................... A01N 43/16
[52] U.S. Cl. ............................................ 71/77; 71/88
[58] Field of Search ................................... 71/88, 77

[56] References Cited

U.S. PATENT DOCUMENTS

| | | | |
|---|---|---|---|
| 4,534,965 | 8/1985 | Brown et al. | 424/93 |
| 4,536,207 | 8/1985 | McCancliss et al. | 71/88 |

FOREIGN PATENT DOCUMENTS

7239035 10/1972 Japan.

OTHER PUBLICATIONS

Koehle et al., Chem. Abst., vol. 100 (1984), 117974v.
Boller et al., Planta, 157:22-31 (1983), "Chitinase in Bean Leaves: Induction by Ethylene, Purification, Properties, and Possible Function".
Mitchell et al., Proc. Soil Sci. Amer., 26, 1962, pp. 556-558, "Microbiological Processes Associated with the Use of Chitin for Biological Control".
Vance et al., Ann. Rev. Phytopathol., 18, 1980, pp. 259-288, "Lignification as a Mechanism of Disease Resistance".
Brown et al., Developments in Industrial Microbiology, 23, 1982, pp. 513-520, "Biologically Treated Shrimp Waste as a Seed Treatment to Control Pathogenic Fungi".
Pearce et al., Physiol. Plant Pathol., 20, 1982, pp. 119-123, "Chitosan and Related Compounds as Elicitors of the Lignification Response in Wounded Wheat Leaves".
Young et al., Plant Physiol., 70, 1982, pp. 1449-1454, "Effect of Chitosan on Membrane Permeability of Suspension-Cultured Glycine Max and Phaseolus ulgaris Cells".
Young et al., *Plant Physiol., 73, 1983, pp. 698-702, "Release of Calcium from Suspension-Cultured Glycine Max Cells by Chitosan, Other Polycations, and Polyamines in Relation to Effects on Membrane Permeability"*.
Haewiger and Adams, Physiol. Plant Pathol., 12, 1978, pp. 63-72, "Nuclear Changes Associated with the Hos-Parasite Interaction between Fusarium solani and Peas".

Allan and Hadwiger, Exper. Mycol., 3, 1979, pp. 285-287, "The Fungicidal Effect of Chitosan on Fungi of Varying Cell Wall Composition".
Nichols and Hadwiger, Phytopathology, 69, 1979, p. 1040, "Enzymes from Pea Tissue Degrade Fusarium solani Cell Walls; Chitosan Fragments both Induce Pisati and Inhibit Fungal Growth".
Hadwiger, Plant Physiol., 63, 1979, No. 5, p. 133, Item 736, "Chitosan Formation in Fusarium solani Macroconidia on Pea Tissue".
Nichols, Beckman and Hadwiger, Plant Physiol., 66, 1980, pp. 199-204, "Glycosidic Enzyme Activity in Pea Tissue and Pea-Fusarium solani Interactions".
Hadwiger and Beckman, Plant Physiol., 66, 1980, pp. 205-211, "Chitosan as a Component of Pea—Fusarium solani Interactions".
Hadwiger Line, Physiol. Plant Pathol., 19, 1981, pp. 249-255, "Hexosamine Accumulations are Associated with the Terminated Growth of Puccinia striiformis on Wheat Isolines".
Hadwiger, Beckman and Adams, Plant Physiol., 67, 1981, pp. 170-175, "Localization of Fungal Components in the Pea-Fusarium Interaction Detected Immunichemically with Anti-Chitosan and Anti-Fungal Wall Anti-Sera".
Hadwiger and Loschke, Phytopathology, II, 1981, pp. 756-762, "Molecular Communication in Host-Parasite Interactions: Hexosamine Polymess (Chitosan) as Regulator Compounds in Race-Specific and Other Interactions".
Hadwiger and Line, Phytopathology, 71, No. 2, 1981, p. 222, "The Presence of 'Chitosan-Like' Compounds in Wheat-Puccinia striiformis Interaction".
Kendra, Hadwiger and Beckman, Plant Physiol., 69, 4 Suppl., 1982, p. 6, "Anti-Fungal Action of Chitosan on Protein and Cell Wall Polymer Synthesis in Fusarium solani".
Walker-Simmons, Ryan and Hadwiger, Plant Physiol., 69, 4 Suppl., 1982, p. 21, "Elicitation of the Phytoalexin Pisatin by the Proteinase Inhibitor Inducing Factor, P11F".

(List continued on next page.)

Primary Examiner—Catherine L. Mills
Attorney, Agent, or Firm—Wegner & Bretschneider

[57] ABSTRACT

Commercially produced chitosan applied to cereal crop seeds at rates of 60 µg to 1000 µg per gram of seed enhances root development, crown diameter, mature straw strength and crop yield. Dry chitosan, when dissolved in dilute acid and neutralized, is applied directly to cereal crop seed with only minor modification to seed treating machinery and methods. In addition to a clear benefit in cereal crop yield, the chitosan treated seed can be planted early to reduce erosion and it can be planted in regions having soil infested with root rotting organisms and not suffer extensive lodging that would prevent seed recovery by commercial harvesters.

15 Claims, No Drawings

OTHER PUBLICATIONS

Wagoner, Loschke and Hadwiger, *Physiol. Plant Pathology*, 20, 1982, pp. 99-107, "Two-Dimensional Electrophorectic Analysis of in Vivo and in Vitro Synthesis of Proteins in Peas Innoculated with Compatible and Incompatible *Fusarium solani*".

Walker-Simmons, Hadwiger and Ryan, *Biophys. Res. Comm.*, 110, 1983, pp. 194-199, "Chitosans and Pectic Polysaccharides both Indua the Accumulation of the Anti-Fungal Phytoalexin Pisatin in Pea Pods and Anti-Nutrient Proteinase Inhibitors in Tomato Leaves".

Hadwiger and Wagoner, *Physiol. Plant Pathol.*, 23, 1983, pp. 153-162, "Electrophoretic Patterns of Pen and *Fusarium solani* Proteins Synthesized in Vitro or in Vivo Which Characterize the Compatible and Incompatible Interactions".

Loschke, Hadwiger and Wagoner, *Physiol. Plant Pathol.*, 23, 1983, pp. 163-173, "Comparison of MRNA Populations Coding for Phenylalanine Ammonia Lyase and Other Pepticles from Pea Tissues Treated with Biotic and Abiotic Phytoalexin Inducers".

Hadwiger, Wagoner and Loschke, *J. Cell. Biol.*, Suppl. 7B, 1983, p. 274, Abstr. 1234, "Accumulation of Messenger RNAs Associated with Biotic and Abiotic Induction of Disease REsistance Proteins in Plants".

1981 *Wheat Research Review*, pp. 63-64, "Evaluation of Chitosan as a Systemic Fungicide".

1982 *Wheat Research Review*, pp. 25027, "Chitosan as a Fungicide and Inducer of Disease Resistance Responses".

1983 *Wheat Research Review*, pp. 27-28, "Evaluation of Chitosan as a Seed Treatment".

Washington Sea Grant Program Project Proposal, Jun. 1, 1979, "Crab Shell Chitosan as a Commercial Fungicide".

Washington Sea Grant Program Project Proposal, Mar. 31, 1980, "Crab Shell Chitosan as a Commercial Fungicide".

Washington Sea Grant Program Project Proposal, Apr. 5, 1982, "Crab Shell Chitosan as a Commercial Fungicide".

Kohle, Young and Kauss, *Plant Science Letters*, 33, 1984, pp. 221-230, "Physiological Changes in Suspension-Cultural Soybean Calls Elicited by Treatment with Chitosan".

Walker-Simmons and Ryan, *Plant Physiol.*, 76, 1984, pp. 787-790, "Proteinase Inhibitor Synthesis in Tomato Leaves".

Stossel and Leuba, *Phytopath. Z.*, 111, 1984, pp. 82-90, "Effect of Chitosan, Chitin and Some Aminosugars on Growth of Various Soilborne Phytopathogenic Fungi".

Kendra and Hadwiger, *Exper. Mycol.*, 8, 1984, pp. 276-281, "Characterization of the Smallest Chitosan Oligomer that is Maximally Anti-Fungal to *Fusarium solani* and Elicits Pisatin Formation in *Pisum sativum*".

Mauch, Hadwiger and Boller, *Plant Physiol.*, 76, 1984, pp. 607-611, "Ethylene Sympton, Not Signal for the Induction of Chitinase and Beta-1, 3-Glucanase in Pea Pods by Pathogens and Elicitors".

Hadwiger, Fristensky and Riggleman, *Chitin, Chitosan and Related Enzymes* (Proc. Jt. U.S.-Jpn. Semin. Adv. Chitin, Chitosan and Related Enzymes) (ed. J. P. Zikakis, Academic Press, 1984), pp. 291-302, "Chitosan, a Natural Regulator in Plant-Fungal Pathogen Interactions, Increases Crop Yields".

Rawis, *Chem. & Eng. News*, 62, May 14, 1984, pp. 42-45, "Prospects Brighten for Converting Chitin Wastes to Valuable Products".

Walker-Simmons, Jin, West, Hadwiger and Ryan, *Plant Physiol.*, 76, 1984, pp. 833-836, "Comparison of Proteinase Inhibitor Inducing Activities and Phytoalexin Elicitor Activities of a Pure Endopolygalactouronase, Pectic Fragments, and Chitosan".

1984 *Washington Wheat Review*, pp. 64-65, "Made of Action of Chitosan in Reducing Disease-Caused Lodging Winter Wheat".

Wahington Sea Grant Program Project Proposal, Jul. 3, 1984, "Chitosan and Enhanced Wheat Yield".

METHOD FOR TREATING CEREAL CROP SEED WITH CHITOSAN TO ENHANCE YIELD, ROOT GROWTH AND STEM STRENGTH

This application is a continuation of application Ser. No. 795,702 filed on Nov. 5, 1985 now abandoned, which is a continuation of application Ser. No. 658,084 filed Oct. 5, 1984, now abandoned.

BACKGROUND OF THE INVENTION

One of the major problems in growing cereal crops (defined as members of the grass family (Graminae) that produce edible, starchy grains and characterized by long, narrow blades) is the lodging (falling over) of plants prior to harvest, which prevents the mechanical recovery at harvest of high yielding plant heads. Researchers have tried to alleviate this problem by:
 1. Breeding stiffer stemmed varieties;
 2. Using chemical treatments such as benzamidazole-type fungicides (Benlate) to reduce root rot;
 3. Recommending that planting dates be delayed so that there is a minimal time for organisms to initiate the root rotting process prior to the slow growth phase of winter; and
 4. Recommending no-till or minimum tillage procedures that leave crop debris to reduce the erosion that is rampant when planting dates are delayed.

Each of these alternative procedures are partial solutions to yield losses. However, each has serious drawbacks.

It has been impossible to breed for straw strength and still retain all of the other agronomic traits, e.g., winter hardiness, milling quality yield, disease resistance, etc., at the same time because the high yielding heads place unusually severe strain on the plant stem.

Lodging has been reduced by fungicides that are derivatives of methyl 1-(butylcarbamoyl)-2-benzimidazole carbamate (Benlate), which reduce the incidence of root rotting and thus retain original straw strength. Extended use of this chemical, however, has resulted in the selection of fungal pathogens that are resistant to its fungicidal effect and, thus, effectiveness is greatly diminished. Only emergency Food and Drug Administration clearance has been obtained for use of this chemical on wheat because of potential side effects. Finally, its cost of treatment (approximately $7/acre) is very high.

Delaying the planting date has reduced lodging; however, it prevents the time dependent development of large seedling plants needed for ground cover prior to the onset of winter rains and erratic snow melts that erode away large tonnages of soil each year. The latter problem can be reduced by minimal tillage practices that leave straw on top of the soil at planting time. However, minimal tillage, which produces generally lower yields, leaves weeds untilled as well and must be accompanied by additional herbicide and pesticide treatments requiring expensive machinery for application.

Accordingly, there exists a need for a method that will increase the straw strength and the root development of cereal crops at a commercially feasible cost while still maintaining or increasing the amount of yield.

SUMMARY OF THE INVENTION

This invention describes a novel chitosan seed treatment that strenghthens the stems of cereal crop plants, such as wheat, helping to preserve their water-carrying capacity and greatly reducing lodging (plants falling over before harvest), thus increasing yield. The lodging problem is most severe when seed is planted early so that the plants can cover the ground prior to the soil eroding winter rains. Thus, by using this seed treatment, farmers will be able to plant crops early and reduce the erosion loss that exceeds 10 tons per acre in some parts of the United States.

While this invention is applicable to any of the cereal crops (e.g., rye, oats, etc.), primary work has been done with wheat and this specification will discuss the invention using wheat as an embodiment.

The problem of lodging of high yielding wheat plants can be rectified by seed treatment with the naturally occurring carbohydrate, chitosan. Commercially produced chitosan when applied in an aqueous form to wheat seeds is able, under field conditions, to greatly increase the development of the plant's root system, to substantially increase the diameter of the stem, and, in association with these specific and other intangible, morphological and biochemical developments, to enhance yield. The chitosan treatment results in a plant that is beneficial to erosion control, resistant to lodging, and superior in yield over non-treated plants. The method of treatment comprises the direct application of chitosan derived from various shell sources, such as crab, lobster, shrimp and other marine life, in a nearly neutral aqueous solution to wheat seeds prior to planting.

Accordingly, it is a primary object of the present invention to provide a method for increasing the straw strength and root development of cereal crops while increasing the amount of yield.

This and further objects and advantages will be apparent to those skilled in the art in connection with the detailed description of the preferred embodiments set forth below.

DETAILED DESCRIPTION OF THE PREFERRED EMBODIMENTS

Chitosan is a polymer made up of a hexosamine sugar (glucosamine) whose molecules are linked ($\beta$1, 4) into chains that can exceed molecular weights of one million. Chitosan compounds in a range of up to and exceeding $1 \times 10^6$ molecular weight are derived commercially from chitin. Chitin, an amino cellulose derivite, is the second most abundant polymer occuring in nature, existing, for example, in the cell walls of fungi, bovine cartilage, and the hard shells of insects and crustaceans. Wastes from the shrimp, lobster, and crab seafood industries contain 10–30% chitin. Chitosan is produced by deacetylating chitin. This invention is effective if the deacetylation exceeds 90% and it is most effective when approaching 100% deacetylation.

Dry chitosan as either flakes, granules, or powder is suitable as a starting material. The more finely dispersed the chitosan, the more quickly it can be dissolved in a dilute aqueous acid (e.g., 1% acetic acid or dilute hydrochloric acid, sulfuric acid, or formic acid).

Typically, a quantity of chitosan suitable for planting a 160 acre field (quarter section) would be mixed as follows: 2.4 lbs. of crab shell chitosan is dissolved in 8 gallons of 1% acetic acid. 48 hours is allowed at room temperature for the chitosan to dissolve with stirring. H₂O is then added to bring the volume to 26 gallons or until the viscosity is reduced enough to feed through the dispenser of commercial seed treating machinery. (Most seed treatment machines utilized to handle water based seed treatments can be utilized with the aqueous solution of chitosan). The solution is neutralized to pH 6.0 to 6.5 with 0.2 to 0.23 gallons of 6.0N NaOH. NaOH is added slowly with stirring, because localized changes to a pH higher than 7.0 will cause the chitosan to precipitate. Once near neutrality, the viscosity of the opaque aqueous preparation of chitosan is reduced to the designed viscosity with H₂O to approximately 26 gallons. From this, approximately 0.125 gallons is added to each bushel of wheat seed. This volume of aqueous chitosan increased the moisture percentage of 60 lbs. of wheat seed by 1.6%.

Chitosan seed treatments were found to be effective using rates ranging from 60 $\mu g$ chitosan per gram of wheat seed to 1000 $\mu g$ chitosan per gram of wheat seed. Optimal results were obtained at 250 $\mu g$ chitosan per gram of wheat seed. This rate is 0.014 lbs. chitosan per 60 lbs. (1 bushel) of wheat. Sixty pounds per acre is the average seeding rate for wheat in most areas.

The native chitosan required to treat seed prior to planting costs less than $0.50/acre. Chitosan treated seed can be planted in late summer or as early in August as moisture is available. The chitosan treatment enhances stem diameter by approximately 10%. Although chitosan-treated plants grown in soils heavily infested with root rotting disease are susceptible to development of some rotting symptoms such as stem discoloration and some white heads, the larger stem diameter and the extensive root system caused by the treatment maintain greater stem strength and an adequate water transporting capacity of stem vascular systems. As a result of seed treatment with this naturally occurring compound, 10–30% higher yields are obtained at a low cost, soil erosion is minimized, and the chitosan is readily degraded to simple amino sugar residues and/or metabolized by soil organisms.

Plants and micro-organisms contain chitosanase and other degradative enzymes with the potential to digest chitosan into smaller fragments and eventually into hexosamines that can be utilized as nutrients by soil microflora.

If seed is treated in a humid environment, a post-treatment drying step must be added to reduce the moisture content of the treated grain to the 10–14% range in order to prevent premature germination of the seed; therefore, the more viscous the chitosan preparation, the less drying that will be required. Highly viscous chitosan preparations can be mixed with wheat seed using any machinery marketed for cement mixing. Modifications of grain augering devices will also enable chitosan to be added to wheat seed as it is being loaded aboard trucks just prior to transport to the field for planting. This eliminates the need for extensive drying to prevent seed germination.

Chitosan seed applications are not detrimentally influenced by fertilizer supplements, herbicide applications or irrigation programs. Other commercial seed treatments, e.g., insecticides and fungicides, can be applied prior to chitosan. Components already on the seed will be attached to the seed by the chitosan, which leaves a "cellophane-like" surface on seed after drying. The chitosan-treated seed can be planted directly in any commercial planter. Special planters that automatically administer fertilizers, soil sterilants, herbicides, etc. can be utilized to treat seeds with chitosan as they are being planted. Chitosan labelled with tritium, [³H]-Chitosan, added to seeds was translocated to the developing plant indicating that a large portion of the chemical is distributed systemically.

Dry chitosan can be stored indefinitely at room temperature without loss of biological activity. Chitosan can be mixed as described above at room temperature. Chitosan has no known toxicity and can be supplemental to the diet of animals without detrimental side effects. The physical irritation properties of chitosan have not been investigated in long term studies, however, and, therefore, the same basic precautions taken in the handling of other fibrous materials or powders, e.g., cotton fibers or flour, may apply to chitosan.

The root enhancing, stem diameter increasing, and strengthening effect of chitosan is seen at both early and late seeding dates; however, the major beneficial effects for erosion reduction are obtained with early seeding dates. This allows the development of the large seedling plants needed for ground cover prior to the onset of winter rains and snow melts while the chitosan minimizes the problem of root rotting.

The following data illustrate examples of enhanced properties obtained, in this case, in wheat through the use of this invention.

EXAMPLE 1

Enhanced Seedling Development

Seedlings from Chitosan treated Daws wheat seed (200 g Chitosan/g seed) 4 months after planting at Washtuchna, Wash. under circle irrigation, Oct. 15, 1983.

| Seed Treatment | Ave. diameter of crown (lower stem) mm | Ave. length of stem from crown to first leaf cm | Ave. wt. root system per 30 plants | |
|---|---|---|---|---|
| | | | fresh wt g. | dry wt g |
| H₂O control | 2.3 | 3.7 | 1.002 | .139 |
| Chitosan (200 $\mu g$/g seed) | 3.7 | 3.8 | 2.690 | .330 |

EXAMPLE 2

Reduced Lodging

Daws winter wheat 1983 crop lodging reading on outside row of 4'×100' plot.

| Treatment $\mu g$ Chitosan/gram seed | Stems lodged No. |
|---|---|
| Chitosan 62 | 275 |
| Control | 468 |
| Chitosan 125 | 313 |
| Control | 948 |
| Chitosan 250 | 143 |
| Control | 835 |
| Chitosan 500 | 186 |
| Control | 652 |
| Chitosan 1000 | 250 |
| Control | 410 |

EXAMPLE 3

Increased Stem Diameter

Effect of chitosan seed treatment on stem diameter of Daws wheat at maturity—1983.

| Chitosan applied per gram seed μg | Stem diameter mm | % increase |
| --- | --- | --- |
| Chitosan 62 | 3.872[a] | — |
| Control | 3.239 | 19 |
| Chitosan 125 | 3.432 | — |
| Control | 3.231 | 6 |
| Chitosan 250 | 3.606 | — |
| Control | 3.322 | 9 |
| Chitosan 500 | 3.997 | — |
| Control | 3.651 | 9 |

[a]Average diameter of 100 stems.

EXAMPLE 4

Enhanced Yield

Effect of Chitosan Seed Treatment on Daws Winter Wheat Yield in 1983

| | CHITOSAN application lbs/bushel | cost acre | Avg. Yield bushels acre | Bushel Increase Per Acre | % increase over control |
| --- | --- | --- | --- | --- | --- |
| Chitosan 1000 μg/g wheat | .059 | $.50[a] | 90.2[b] | 11.4 | 14% |
| Control | | | 78.8 | | |
| Chitosan 500 μg/g wheat | .029 | $.25 | 89.7 | 10.9 | 13% |
| Control | | | 77.8 | | |
| Chitosan 250 μg/g wheat | .014 | $.12 | 94.3 | 16.5 | 21% |
| Control | | | 84.2 | | |
| Chitosan 125 μg/g wheat | .007 | $.06 | 91.5 | 7.3 | 8% |

[a]Dollar values were: chitosan (lbs)/60 lbs. seed (planting rate/acre) × 160 acres × $9.00/lb. chitosan.
[b]Yield was an average of four replications. Plot size was 4' × 30'. Lodging in control plots was up to 60%. Yield included lodged wheat recovered by hand at harvest.

EXAMPLE 5

Enhanced Yield

| Fielder spring wheat treatment 1982 | yield - % of control |
| --- | --- |
| Chitosan (320 μg/g) seed treatment only | 131 |
| Control | 100 |

EXAMPLE 6

Enhanced Yield

| Daws winter wheat treatment - 1982 | yield - % of control |
| --- | --- |
| Chitoson (500 μg/g) seed treatment | 107 |
| Control | 100 |

EXAMPLE 7

Enhanced Disease Resistance

Effects of Chitosan Seed Treatment.
Daws Wheat *Psuedocercosporella herpotrichoides.*
Disease symptoms on wheat straw at harvest.
No. of Straws/Sympton Value Category (Chitosan treatment and control).

| Mature Stem Symptoms Symptom Value | Clean Straw 0 | Slight Discoloration 1 | Scattered Lesions 2 | Coalescing Lesions 3 | Diseased & Broken 4 |
| --- | --- | --- | --- | --- | --- |
| 62 μg/g | 4 | 22 | 35 | 22 | 17 |
| Control | 8 | 28 | 40 | 24 | 8 |
| 125 μg/g | 5 | 13 | 24 | 12 | 46 |
| Control | 1 | 8 | 21 | 49 | 21 |
| 250 μg/g | 2 | 15 | 19 | 48 | 18 |
| Control | 0 | 8 | 39 | 48 | 5 |
| 500 μg/g | 7 | 19 | 37 | 21 | 16 |
| Control | 0 | 4 | 35 | 59 | 7 |
| 1000 μg/g | 0 | 8 | 32 | 55 | 5 |
| Control | 1 | 9 | 38 | 48 | 4 |

Having fully described the present invention, it will be apparent to those skilled in the art that modifications to the method described herein may be made without departing from the scope of the present invention. While the embodiment described involves wheat, the process is generally applicable to cereal crops. Only the wheat embodiment has been included for the sake of brevity. Therefore, the scope of this invention is not intended to be limited except as may be required by the lawful scope of the following claims.

What is claimed is:

1. A method of enhancing stem diameter and root development in wheat plants comprising the step of applying chitosan in an effective amount to wheat seed prior to planting wherein the rate of application of the chitosan is between 60 μg per gram of wheat seed and 1000 μg per gram of wheat seed.

2. The method of claim 1 wherein the chitosan is dissolved in a dilute aqueous acid solution prior to application.

3. The method of claim 1 wherein the rate of application of the chitosan is between 225 $\mu$g per gram of wheat seed and 275 $\mu$g per gram of wheat seed.

4. The method of claim 3 wherein the rate of application of the chitosan is about 250 $\mu$g per gram of wheat seed.

5. A method of enhancing straw strength, stem diameter, and root development in wheat plants comprising the step of applying chitosan in an effective amount to wheat seed, the chitosan being produced by deacetylating chitin to an extent exceeding 90%.

6. The method of claim 5 in which chitosan is applied to the wheat seed as a dilute neutralized aqueous acid solution of chitosan.

7. The method according to claim 5 in which the dilute aqueous acid for the solution of chitosan is selected from the group consisting of acetic acid, hydrochloric acid, sulfuric acid, and formic acid.

8. The method according to claim 6 in which the solution of chitosan is neutralized to a pH no greater than 7.0.

9. The method according to claim 8 in which the dissolved chitosan solution is neutralized to a pH of 6.0 to 6.5.

10. The method according to claim 6 in which the application of chitosan to the wheat seed leaves a cellophane-like surface on the wheat seed after drying.

11. The method according to claim 10 in which the rate of application of the chitosan is between 60 $\mu$g per gram of wheat seed and 1000 $\mu$g per gram of wheat seed.

12. The method according to claim 11 in which the rate of application of the chitosan is between 225 $\mu$g per gram of wheat seed and 275 $\mu$g per gram of wheat seed.

13. The method according to claim 12 in which the rate of application of the chitosan is about 250 $\mu$g per gram of wheat seed.

14. A method of preventing lodging of wheat plants comprising the steps of:
a. dissolving in a dilute aqueous acid chitosan that has been produced by deacetylating chitin to an extend exceeding 90%, in order to form an aqueous acid solution of chitosan;
b. neutralizing the aqueous acid solution of chitosan to a pH no greater than 7.0;
c. coating wheat seed with the neutralized aqueous acid solution of chitosan; and
d. drying the wheat seed to leave a cellophane-like surface of chitosan on the wheat seed.

15. The method according to claim 14 in which the rate of application of chitosan is between 60 $\mu$g per gram of wheat seed and 1000 $\mu$g per gram of wheat seed.

* * * * *